United States Patent [19]
Dunleavy et al.

[11] Patent Number: 6,042,909
[45] Date of Patent: Mar. 28, 2000

[54] ENCAPSULATION DEVICE

[75] Inventors: Karen E. Dunleavy, Billerica; Timothy J. Perlman, Lexington; Kerry A. Gagnon, Danvers; Claudy J. P. Mullon, Framingham, all of Mass.

[73] Assignee: Circe Biomedical, Inc., Lexington, Mass.

[21] Appl. No.: 08/922,910

[22] Filed: Sep. 3, 1997

[51] Int. Cl.[7] .............................. A61K 9/22; A61M 31/00; C12M 1/00; C12N 5/00
[52] U.S. Cl. ...................... 428/35.7; 128/898; 206/524.7; 206/828; 424/9.1; 424/9.2; 424/422; 424/423; 424/424; 424/DIG. 7; 428/36.6; 428/36.9; 428/200; 428/347; 428/355 N; 428/424.6; 428/424.7; 435/395; 435/400; 435/401; 435/402; 604/57; 604/891.1
[58] Field of Search ................................ 428/35.2, 35.7, 428/36.6, 36.9, 200, 347, 355 N, 424.6, 424.7; 424/9.1, 9.2, 422, 423, 424, DIG. 7; 206/438, 524.1, 524.68, 524.7, 828; 604/891.1, 892.2; 623/113; 525/937; 128/898; 435/395, 400, 401, 402

[56] References Cited

U.S. PATENT DOCUMENTS

| | | | |
|---|---|---|---|
| 5,639,275 | 6/1997 | Baetge et al. | 604/891.1 |
| 5,653,687 | 8/1997 | Mills et al. | 604/57 |
| 5,653,688 | 8/1997 | Mills et al. | 604/57 |
| 5,713,887 | 2/1998 | Mills et al. | 604/890.1 |
| 5,738,673 | 4/1998 | Mills et al. | 604/891.1 |
| 5,773,286 | 6/1998 | Dionne et al. | 435/297.1 |
| 5,786,216 | 7/1998 | Dionne et al. | 435/402 |

FOREIGN PATENT DOCUMENTS

WO 94/25074  11/1994  WIPO.

OTHER PUBLICATIONS

Aebischer et al., "Functional Recovery in Hemiparkinsonian Primates Transplanted with Polymer–Encapsulated PC12 Cells," *Exper. Neurol.*, 126:151–158, 1994.

Allen et al., "Evaluation of Anti–AIDS Drugs in Conventional Mice Implanted with a Permeable Membrane (Hollow Fiber) Device . . . ," abstract, Int'l Soc. Antiviral Research, 8th Int'l Conf., Santa Fe, NM, 1995.

Altman et al., "Successful Pancreatic Xenografts Using Semipermeable Membrane," *Artificial Organs,* 5(Suppl):776–779, 1981.

Hollingshead et al., "In Vivo Drug Screening Applications of HIV–Infected Human Cells Cultivated in Hollow Fibers," Am. Soc. Microbiol. Human Retroviruses & Related Infections, 2nd Int'l Conf., item 496:146, 1995.

Joseph et al., "Xenotransplantation of Encapsulated Bovine Chromaffin Cells in the Sheep Subarachnoid Space . . . ," abstract #128, *Cell Transplantation,* 2nd Int'l Cong. Cell Trans. Soc., 3(3):243, 1994.

(List continued on next page.)

*Primary Examiner*—Ellis Robinson
*Assistant Examiner*—Sandra M. Nolan
*Attorney, Agent, or Firm*—Fish & Richardson P.C.

[57] ABSTRACT

The invention features an empty device for receiving a bioactive agent. The device includes a biocompatible and semi-permeable membrane that defines an enclosed space; the membrane also has at least one end that defines an opening for introducing the bioactive agent into the enclosed space. The device is configured to be placed in an animal.

In one embodiment of the invention, the membrane has an inner surface and an outer surface, where the inner surface defines the inner surface, and includes a biocompatible adhesive in the general region of the opening to allow sealing of the opening after the introduction of the bioactive agent into the enclosed space.

Another embodiment of the invention includes a biocompatible frame mounted in supporting relationship to the membrane and defining an opening for introducing the bioactive agent into the enclosed space. The frame has greater porosity than the membrane.

3 Claims, 1 Drawing Sheet

OTHER PUBLICATIONS

Lacy et al., "Maintenance of Normoglycemia in Diabetic Mice by Subcutaneous Xenografts of Encapsulated Islets," *Science*, 254:1782–1784, 1991.

Lanza et al., "Xenotransplantation of canine, bovine, and porcine islets in diabetic rats without immuno–suppression," *Proc. Natl. Acad. Sci., U.S.A.*, 88:11100–11104, 1991.

Maki et al., "The Biohybrid Artificial Pancreas for Treatment of Diabetes in Totally Pancreatectomized Dogs," *Transplantation Proc.*, 23(1):754–755, 1991.

Maki et al., "Successful Treatment of Diabetes with the Biohybrid Artificial Pancreas in Dogs," *Transplantation*, 51(1):043–051, 1991.

Sullivan et al., "Biohybrid Artificial Pancreas: Long–Term Implantation Studies in Diabetic, Pancreatectomized Dogs," *Science*, 252:718–721, 1991.

Yang et al., "Hollow Fibers for Hepatocyte Encapsulation and Transplantation: Studies of Survival and Function in Rats," *Cell Transplantation*, 3(5):373–385, 1994.

Tecoflex specification sheet for Medical Grade Aliphatic Polyurethanes, Thermedics, Inc., Woburn, MA, 1982.

ENCAPSULATION DEVICE

FIELD OF THE INVENTION

This invention relates generally to encapsulation devices. Specifically, the invention is related to devices that serve as receptacles for receiving bioactive agents.

BACKGROUND OF THE INVENTION

The initial screening of bioactive agents, e.g., drug candidates, has typically been implemented in vitro. Although in vitro tests are practical, they often result in inaccurate data. Drugs that require metabolic activation are among the most promising therapeutic agents, for example, for use as anticancer drugs or antibiotics. However, these drugs can fail in in vitro tests, as the in vitro test systems often do not include all of the necessary enzymes, antibodies, and other compounds required for metabolic activation. Such drugs could therefore be abandoned without further investigation, regardless of their potential efficacy in an intact organism, simply because the in vitro studies might not unerringly mimic in vivo conditions. Likewise, a drug that is highly effective in vitro might not be viable in an organism if, for example, it is degraded or rendered toxic within the cell before reaching its target.

Previous in vivo tests of drug candidates have involved subdermal, subrenal, or peritoneal surgical implantation of a target cell line into a host animal, followed by administration of the drug candidate. Such studies can be misleading, however, as it is often difficult to account for interactions between the implanted cells and the cells of the host. For a similar reason, current in vivo studies are generally limited to the implantation of only a single target cell line into each host. Indeed, since the host animal generally must be sacrificed in order to recollect the implanted cells for analysis, such studies are often precluded by cost considerations, especially in higher mammals.

Examples of healthy cells include pancreatic islet tissue used in artificial pancreas devices. In other examples, Aebischer has implanted dopamine secreting neural cells for the treatment of Parkinson's disease (*Exper. Neurology*, 126:1–8, 1994) and encapsulated bovine chromaffin cells in sheep subarachnoid for the treatment of pain (*Cell Transplantation*, 3:243, 1994).

SUMMARY OF THE INVENTION

In general, the invention features a device for receiving one or more bioactive agents, such as healthy, infected, or malignant cells, enzymes, or infectious agents. The device includes one or more biocompatible and semi-permeable membranes and a frame or adhesive to enable the sealing of the device.

An embodiment of the invention features an empty device for receiving a bioactive agent. The device includes a biocompatible and semi-permeable membrane having an inner surface and an outer surface, where the inner surface defines an enclosed space; the membrane also has at least one end that defines an opening for introducing the bioactive agent into the enclosed space; a biocompatible adhesive in the general region of the opening to allow sealing of the opening after the introduction of the bioactive agent into the enclosed space. The device is configured to be placed in an animal.

The biocompatible adhesive can be, for example, a heat sealable polymer conduit extending beyond the end of the membrane for a length sufficient for heat sealing the conduit without causing the membrane to be contacted in the heat sealing process. The conduit in this example overlaps with and is secured to a terminal portion of the outer surface of the membrane.

The membrane can have a second end that defines an opening, in which case the device also includes a second heat sealable polymer conduit extending beyond the second end.

The heat sealable polymer conduit or conduits can be made of polyurethane, for instance.

The membrane can be in the form of a preformed bag. Examples of bags include bullet-shaped devices, balloons, and cylindrical tubes having one end closed and one end remaining open.

In regard to any of the devices, the membrane can be made of a copolymer of acetonitrile and vinyl chloride. The membrane can have, for example, a hydraulic permeability of 8–70 ml/min/m$^2$/mmHg and a molecular weight cut-off value of 20–150 Kdal.

Another embodiment of the invention features a second device for receiving a bioactive agent. The device features a biocompatible and semi-permeable membrane defining an enclosed space; and a biocompatible frame mounted in supporting relationship to the membrane and defining an opening for introducing the bioactive agent into the enclosed space. The frame has greater porosity than the membrane; and the device is configured to be placed in an animal.

The device can also include a biocompatible member that seals the opening. The member can be formed of a resilient material, for example.

In some cases, the member also includes an outer component of a first material and an inner component of a second material having a different hardness from the first material. The outer component is inserted into the opening and has an orifice for snugly receiving the inner component.

The frame can be in the form of a porous cylinder.

In regard to any of the devices, the membrane can be made of a copolymer of acetonitrile and vinyl chloride. The membrane can have a hydraulic permeability of 8–70 ml/min/m$^2$/mmHg (or even 25–50 ml/min/m$^2$/mmHg) and a molecular weight cut-off value of 20–150 Kdal.

The term "biocompatible" refers to the property of not inducing fibrosis, inflammatory response, host rejection response, or cell adhesion, following in vivo implantation. What is meant by "fibrosis" is tissue growth encapsulating the device.

An animal can be a human or a non-human animal such as a mouse, monkey, dog, rat, monkey, goat, reptile, bird, or guinea pig.

A biocompatible member can be, for example, a plug that is inserted into the opening of the device or a cap that fits over the end of the device to block the opening.

Semi-permeable membranes allow molecules smaller than a predetermined size (i.e., the molecular weight cut-off, or "MWCO") to pass freely from one side of the membrane to the other. In the present invention, the MWCO of all membranes were determined by single protein rejections. The rejection percentages indicated are the percentage of protein that is retained by the membrane (i.e., does not pass through the pores).

Pore size is not easily defined, as there is always a broad range of pore sizes on a given membrane skin. Proteins often interact with the pores in the polymer skin, leaving a deposit that can act as a secondary boundary or rejecting layer. The thickness of the layer varies with, for example, the hydrophobicity of the polymer, the type of protein and the flow properties of the solution (pressure and shear rate) challenging the membrane. For MWCO measurement, a series of single solutes (i.e., typically spherical proteins of various sizes) are used in rejection testing. Smaller proteins pass through the pores (low rejection by the skin) while larger proteins are mostly retained (high rejection). By plotting the rejection curve against the molecular weight of the proteins used as solutes, the MWCO can be deduced.

Hydraulic permeability is defined as the volume of water that can flow through a porous substance per unit of time per unit of surface area per unit of water pressure; thus it can be measured in units of ml/min/m$^2$/mmHg. It is measured by forcing clean water (e.g., water for injection, U.S.P., or "WFI") having a known pressure through a sample of the substance having known dimensions, then measuring the volume of water that emerges from the opposite face of the material after a prescribed length of time has elapsed.

Lengths of the membranes can be sealed into a cylindrical device in which the membranes' inner lumens are separated from the outer membrane surfaces and a chamber is formed between the outer surface of the membranes and the device. The outer chamber is referred to as the "shell side." Water or protein solutions, or both, are passed through the inner lumens of the membranes in the devices. The pressure applied by the solutions is controlled and is referred to as the "transmembrane pressure." While most of the solution is recirculated through the membrane lumens, a portion will cross the membrane wall to the shell side. A peristaltic pump can be used to drive the flow. The solution is drawn from a reservoir, through the pump to an inlet, through the lumens of the membranes, out of the device through an outlet, and back into the reservoir, thereby recirculating the solution. The rate of the fluid (sec$^{-1}$) over the inner membrane surface is usually regulated, as is the pressure applied to the surface. The pressure can be regulated (e.g., with a clamp on the outlet tubing) such that the pressure drop across the device is minimized.

For clean water, the rate (volume/time) of passage through the walls is referred to as the flux, or normalized permeability (volume/time/surface area/pressure). When proteins of known size are used as markers, dilute solutions are prepared and recirculated as described above in the context of MWCO determination. The percentage of protein that remains recirculating in solution and does not cross the membrane wall is referred to as the percent protein rejection. Generally, a series of proteins of known molecular weight and similar shape are used.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present application, including definitions, will control. In addition, the materials, methods, and examples are illustrative only and not intended to be limiting.

An advantage of the devices is ease of use. The new devices facilitate the introduction of bioactive material into a host and, subsequently, the recovery of that material without sacrificing the host.

There are also advantages that pertain more particularly to devices that have at least one heat sealable polymeric conduit extending beyond the ends of the membrane: 1) there is little, if any, damage to the membrane structure when heat sealing the conduits; 2) there are no toxic adhesives necessary; such compounds could potentially contaminate the cells; 3) the conduits are generally homogenous films, which heat seal reproducibly and create an effective barrier against leakage; 4) the conduits can be made of materials (e.g., polyurethane) that are fairly free of tissue growth or fibrosis; and 5) because it is the conduit, not the membrane, that is heat sealed, the membrane characteristics (e.g., MWCO, hydraulic permeability, and porosity) are unaffected.

Other features and advantages of the invention will be apparent from the following drawings, the detailed description, and from the claims.

DETAILED DESCRIPTION OF THE INVENTION

The invention relates to a biocompatible device prepared from a semi-permeable membrane in the form of a tube or bag, having at least one opening and either a supporting frame or an adhesive in the vicinity of the opening, or both. A semipermeable membrane can be selected that allows, for example, drugs to pass freely through the membrane but infectious agents and cells to remain trapped within the device. The frame and the adhesive each facilitate the sealing of openings in the membrane after the bioactive materials have been added. The frame additionally provides the membrane with rigidity and support. The device can be used for implantation of bioactive agents, such as whole cells, cell extracts, infectious agents, or enzymes.

Any implantable device may not be suitable for this purpose. For example, selection of a membrane with a low molecular weight cutoff (MWCO) is critical if prevention of an immune response against the implanted cells is desired. Also, a smooth exterior surface, one that does not promote fibrosis or foreign body response, can be important if longer periods of implantation are necessary.

One example of a suitable membrane is double-skinned and has smooth inner and outer surfaces. The interior portion of the membrane (i.e., in between the inner and outer skins) is highly porous and spongy. The double skinned membranes have the advantage of being strong but not stiff, compared with single skinned membranes, for example.

Figure 1:
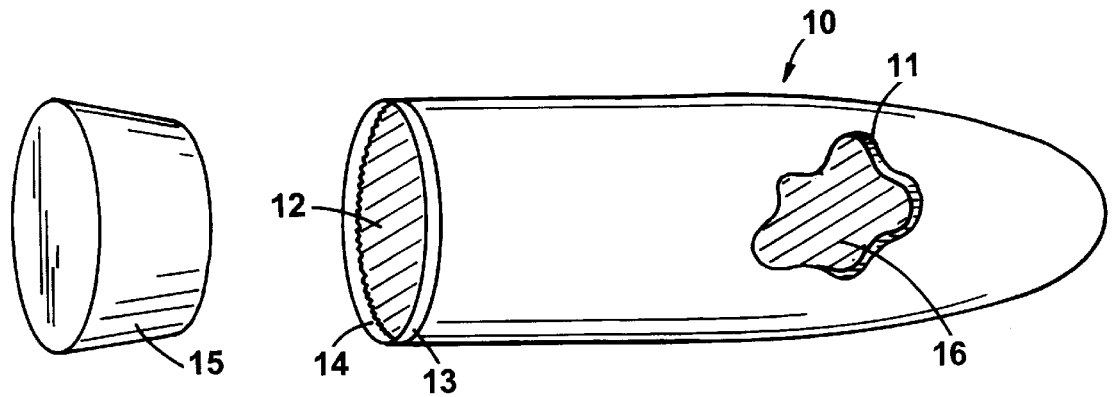
FIG. 1 is a diagrammatic view of an encapsulation device of this invention in the form of a bullet-shaped bag.

In FIG. 1, an encapsulation device 10 is illustrated. The device 10 includes a membrane 11, an adhesive 14, and a sealing member 15 that seals the device. The bag-like shape of the membrane 11 defines a continuous enclosed space 16 on the inside of the "bag," i.e., the membrane itself defines the bag-shaped space 16, without the need for an adhesive or an additional member. The membrane 11 also defines an opening 12, the mouth of which is a rigid or semi-rigid frame 13. The inside rim of the frame 13 is coated with the adhesive 14, which holds the member 15 in place. The rim can be made, for example, of a solid plastic (e.g., PAN/PVC or acrylic) or a metal (e.g., stainless steel or titanium). The member 15 is made from a resilient, self-sealing substance (e.g., rubber, silicone, or another polymer) that allows materials to be added to the space 16 (e.g., with a needle or cannula penetrating through member 15), even after the membrane 15 has been sealed in place with the adhesive 14.

A device identical to that depicted in FIG. 1, without the rigid frame 13 or member 15, is also within the scope of the claims. Such a device would be sealed with an adhesive or by heat sealing after the cells or other materials are added.

Figure 2:
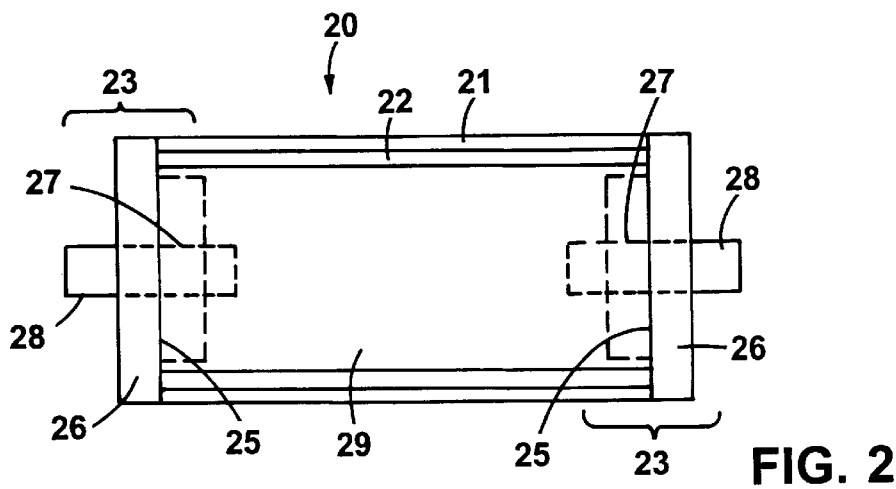
FIG. 2 is a plan view of another encapsulation device of this invention including a frame that defines two openings.

Another framed device 20 is shown in FIG. 2. A membrane 21 surrounds rigid but porous frame 22, which reinforces the device. The frame 22 defines an enclosed space, or lumen 29, and openings 25, which are designed to receive plugs 23. The plug 23 is made up of an outer plug 26 and an inner plug 28. The outer plug 26 fits into the opening 25, and can be held in place with adhesive if necessary.

The inner plug 28 is made of a material that differs in hardness from the material of the outer plug 26, and fits snugly into a hole 27 in the outer plug. For example, the outer plug 26 can be made of silicone and the inner plug 28 might be a rod or other rigid member. The inner plug can be made of any rigid, biocompatible material, such as a polymer. The outer plug can have a pre-formed axial hole and the hole should preferably slightly smaller than the inner plug.

As FIGS. 1 and 2 illustrate, the frame can be a hoop at an end of the device 13 (FIG. 1), or a continuous tube 22 (FIG. 2). The latter design can provide rigidity and facilitate handling. Various hybrids of these two limiting designs are also possible.

The cells are removed by cutting the membrane or by removing the plug from the end of devices having a plug. Cutting the membrane is generally more effective if a very accurate cell count or analysis is desired.

In connection with the devices depicted in FIGS. 1 and 2, the plugs 26 and 28 or sealing member 15 can be removable or non-removable. If they are non-removable, needles (e.g., non-coring needles) can be inserted through the sealing member or plug to allow materials to be introduced or removed from the device.

Figure 3:
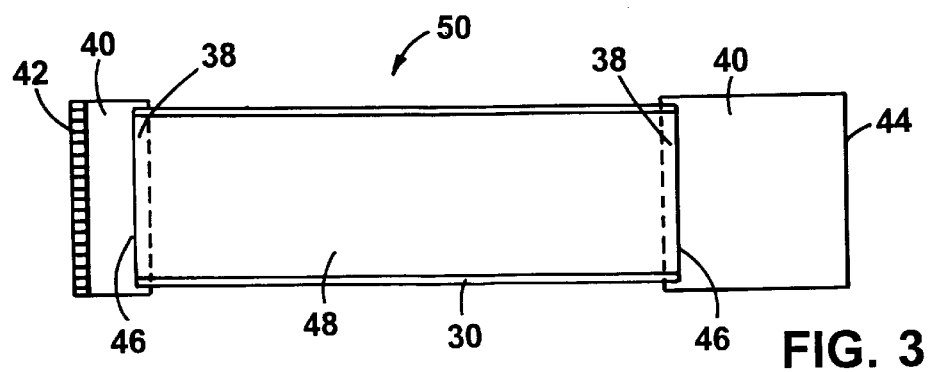
FIG. 3 is a plan view of an encapsulation device having heat sealable conduits at the ends of the membrane.

FIG. 3 shows a non-rigid device 50 having two polymer conduits 40 that extend beyond the ends 46 of a membrane 30 far enough that the conduits 40 can be heat sealed without contacting or damaging the membrane 30. The conduits 40 create an overlap 38 with each end of the membrane 30. The overlap 38 is of sufficient length that the conduits remain securely attached to the outer surface of the membrane 30.

The device 50 of FIG. 3 is shown with the end of one conduit 40 closed with a heat seal 42. A lumen 48 is defined by the bag-like shape formed by the membrane 30 and the heat sealed conduit end 42. The end 44 of the other conduit 40 is left open to allow the device to be filled with, for example, cells, cell extracts, or infectious agents; after filling, end 44 can also heat sealed.

Cells, cell extracts, or infectious agents can be encapsulated in these devices and implanted into an animal (e.g., a human or a non-human animal such as a monkey, mouse, or guinea pig). The animal can be treated with a drug in order to determine the effects of that drug on the encapsulated material. When the experiment is complete, the device can be removed from the animal and the materials within the device can be reisolated by cutting the device open.

Examples of cells that could be encapsulated for drug screening experiments include, but are not limited to, cells from tumors such as melanoma, lung tumors, renal tumors, colon tumors, prostate tumors, ovarian tumors, breast tumors, central nervous system tumors, lymphoma, or leukemia; cells infected by viruses such as cytomegalovirus, herpes simplex virus, rhinovirus, hepatitis A virus, hepatitis B virus, human immunodeficiency virus (HIV), simian immunodeficiency virus, feline immunodeficiency virus, or adenovirus; cells infected by bacteria, yeast, fungi; plant cells; bacteria; yeast; and fungi.

Healthy cells can also be encapsulated. Healthy cells that produce and excrete a therapeutic substance, for example, can be implanted for therapeutic purposes.

Because the semipermeable membranes provide a barrier to cells and infectious agents, devices containing materials that are incompatible with the materials in other devices can be implanted without the attendant complications that would ordinarily arise from the interaction between these materials if they were not encapsulated. For example, a device containing healthy cells can be implanted together with a device containing HIV-infected cells without the possibility of cross-infection. Implantation of a multiplicity of devices into a single animal is therefore feasible. Such a procedure would permit the screening of a single drug against multiple targets in a single host, for example.

Moreover, several devices each containing the same infectious agents or cells can be implanted in different organs or tissues of a single animal, enabling the differential determination of a drug's ability to reach these various organs and tissues.

Without further elaboration, it is believed that one skilled in the art can, based on the above description, utilize the present invention to its fullest extent. The materials, methods, examples, and the specific embodiments are, therefore, to be construed as merely illustrative, and not limitative of the remainder of the disclosure in any way whatsoever.

Cylindrical Device

A 12% polyurethane/acetic acid (PU/AA) solution was prepared as follows. Pellets of type 85A polyurethane, a medical grade, thermoplastic aliphatic polyurethane purchased from Thermedics (Woburn, Mass.), were dried at 60° C. for a minimum of 4 hours. The pellets were weighed out into a clean jar and 88 grams glacial acetic acid U.S.P. was added per 12 grams of pellets. A teflon lid was secured to the mouth of the jar and the jar was placed on a roller mill for a minimum of 16 hours, until all of the pellets were dissolved.

Sintered polyethylene tubes (medical grade, 3.3 mm outer diameter, 0.52–0.54 mm walls) were prepared for use as follows. The tubes were cut squarely using a fresh razor to a length of 14.0–14.5 mm. A 1.5 mm band of the 12% PU/AA solution prepared above was applied to each end of the tube, coating the entire cut ends to soften roughness of the edges. The polyurethane was allowed to cure for 1.5 hours. A 10 cc syringe was then filled with silicone (e.g., Dow Corning medical grade silicon-A, Midland, Mich.; or NU-SIL Corp. MED1137, Carpinteria, Calif.). The syringe's applicator tip was cut to closely match the inner diameter of the polyethylene tube. The silicone was applied to a depth of 2.2–2.5 mm into each end of the sintered tube to form silicone plugs. To minimize variations between the devices, care was taken to ensure that the silicone plugs were not allowed to extend beyond the ends of the tube.

The membranes were prepared by the following wet spinning process (also known as precipitation process). A casting solution was prepared by dissolving an acrylonitrile-vinyl chloride copolymer (KANEKA™ KLR resin, New York, N.Y.) in N-methylpyrrolidone ("NMP"). Water was added to slow the precipitation of the copolymer from the NMP solution during the extrusion process, thereby increasing pore size in the resulting membranes.

The casting solution was extruded through the outer portion of a double annulus nozzle. A precipitating solution made from an NMP-water mixture was pumped through the inner portion of the nozzle. The coextruded membranes are allowed to drop into a coagulating bath, also an NMP-water mixture, where they remained until fully set. The resulting double-skinned membranes were then washed with water and ethanol to remove most of the residual solvent. The washed membranes were dried with glycerine.

The enclosed space defined by the membrane had an inner diameter of 3.5–3.75 mm and the membrane wall thickness was 100 $\mu$m. The membranes were determined to have a hydraulic permeability of 25 ml/min/m$^2$/mmHg (supra) and a MWCO in the range of 50–80 kdal as determined by single protein rejections: bovine serum albumin (67 Kdal) rejection, 50%; and IgG (150 Kdal) rejection, 100%.

Membranes were cut squarely to 13.5 mm length, using necessary caution to ensure a clean, non-feathered cut. The glycerine was removed from each end of the membrane by touching the end to a foam square saturated with 200 proof ethanol for a period of 3 minutes. The wetted length did not exceed 2 mm.

The membrane was allowed to dry for 10–60 min, then slid over the sintered polyethylene tube. When the membrane was centered on the tube, it was then sealed in place by applying a band of PU/AA solution with a syringe fitted with a fine-tipped applicator. The band was uniformly extended from the treated end of the membrane to the treated tube end. The polyurethane was allowed to cure for 1.5 hours.

Two additional applications of PU/AA were made with 1.5 hour cures between applications. After the final application, the polyurethane was allowed to cure for a minimum of 16 hours.

To prepare the devices for shipment, the following procedure was employed to remove the remaining glycerine. A non-coring needle (22 g huber) was inserted through each silicon plug, taking care not to stab into the polyethylene tube. A 10 cc syringe filled with water for injection (WFI) was attached to one of the needles. About 5 ml of WFI was flushed through the inner lumen of the device. The syringe was removed, leaving the needles in place.

The devices were then placed in 10 ml centrifuge tubes. The tubes were filled with WFI and capped. After about one hour, the tubes were drained and the device lumens were flushed with fresh WFI. The tubes were refilled with fresh WFI and allowed to sit for another 1.5 hours. This procedure was repeated for a total of five exchanges.

Leaving the needles in place, the tubes were capped and sealed in plastic bags. The bags were double heat sealed and the bags and their contents were subjected to gamma sterilization (exposure range: 2.5–4.0 Mrads). The devices were removed from the tubes and the WFI was replaced with cells by attaching a filled syringe filled with the cells to one needle and injecting, using the other needle as a vent.

Intraperitoneal Implantation of CEM Cells into Swiss Mice

In one example, CEM cells were encapsulated and implanted intraperitoneally in Swiss mice, according to the following procedure.

The CEM cells were passaged the day before encapsulation. The cells were counted and suspended at 1×10$^5$ cells/ml. 80 $\mu$l of the cell suspension (i.e., approximately 8000 cells) was placed in the lumen of each of several of the devices. The open end of the lumens were heat sealed and further treated by application of polyurethane solution.

The mice were anesthetized with ketamine-xylazine. Eye lubrication was applied to prevent them from drying out. The surgical site was prepared by first clipping away the hair surrounding the site, then sanitizing with a povidone-iodine scrub. Sterile instruments were used to make incisions of approximately 1 cm length in the ventral midline abdominal skin and musculature, and then through the peritoneum.

The encapsulation devices were implanted into the peritoneum of each of three mice for each observation, and the incisions in the peritoneum and skin were closed separately with sutures. The devices were removed on days 4 and 8 post-surgery. The devices were cut open with a scalpel, the cells were retrieved and fixed in formalin, processed by standard histological techniques, and stained with hematoxylin-eosin. Cells were counted using a tryptan blue staining technique, and cell viabilities were determined.

The cells grew very well, with greater than 70-fold increase in count by day 8, at which time more than 93% of the cells remained viable. The membranes of the devices remained normal in appearance with few mouse cells on the outside for the first 4 days. The contents of one device were placed into the well of a microtiter plate in order to observe the cells microscopically. By the eighth day, there was an accumulation of fibrin especially on the tips of the devices. On each day, aggregates of small murine cells were found to have penetrated at least one of the devices. The data resulting from devices contaminated with murine cells were not used for analysis.

The contamination was thought to be due to inadequate sealing of the devices. The "second generation" devices have therefore been designed with heat-sealable polymer conduits at the ends of the devices' membranes.

Intraperitoneal Implantation of HIV-Infected CEM Cells into Swiss Mice

The procedure described above was repeated, with the added step of inoculating the cells with the RF strain of HIV-1 (at a multiplicity of infection, "MOI," of 0.001 or 0.0005) prior to encapsulation. 80 $\mu$l volumes of the virus-infected cells were again encapsulated in the devices, heat sealed, and peritoneally implanted into mice.

The devices were surgically removed at days 4, 6, and 8 post-surgery. The cell suspensions from the devices were placed in wells of microtiter plates and observed microscopically. The cells were observed for contaminating mouse cells and virus induced cytopathic effect. Virus replication was evaluated by measuring p24 antigen on the samples obtained from the devices after removal from the mice. The p24 antigen was measured using a commercially available ELISA kit (Coulter Diagnostics, Miami, Fla.) with the manufacturer's use instructions being explicitly followed. These instructions are incorporated by reference.

When the higher dose of virus (0.001 MOI) was used to infect the CEM cells, an extensive cytopathic effect was noted on day 4. Essentially all of the cells showed cytopathic effect on the sixth day, and the cells had disintegrated by day 8. The infection caused by the lower dose of virus (0.0005 MOI) progressed more slowly, with less cytopathic effect, but the cytopathic effect still reached nearly 100% by the eighth day.

The progression of infection in CEM cells implanted intraperitoneally in the encapsulation devices in mice was determined to be similar to that previously seen in a similar infection set up in vitro.

Measurement of HIV Infection via Measurement of MTT dye Conversion

MTT is a bright yellow tetrazolium dye (3-[4,5-dimethylthiazol-2-yl]-2,5-diphenyltetrazolium bromide) that is taken up by live cells and metabolized to form an insoluble, dark purple formazan product (Cancer Res. 51:1247, 1991. The stained cells are subsequently lysed and the dye is released into the medium. The optical density of each sample is determined using a microplate reader at a wavelength of 570 nm. The optical density value obtained is a function of the amount of formazan produced, which is proportional to the number of viable cells.

An experiment was performed to determine whether or not infection of HIV-inoculated CEM cells could be measured using an MTT dye conversion technique that measures cell viability and virus-induced cell killing. This type of assay is often used in the in vitro evaluation of new anti-HIV drugs and materials. In the experiment, uninfected cells were used as "cell controls" and infected but untreated cells were used as "virus controls."

The infected cells were prepared and implanted as described above. The devices were collected on the sixth day after implantation. The cell suspensions from the devices were placed in wells of microtiter plates and observed microscopically. The cells were again observed for contaminating mouse cells and virus induced cytopathic effect. The higher dose of virus (0.001 MOI) had produced 100% cytopathic effect and the lower dose of virus (0.0005 MOI) had produced about 40% cytopathic effect.

60 $\mu$l samples were analyzed using MTT. The optical density ("O.D.") for the cell control was 1.238, which would be considered a normal value in an in vitro assay. The O.D. of the high concentration of virus was 0.333. The differential (1.238–0.333) of 0.905 is considered an adequate value to allow determination of drug/test material activity. It was concluded that the MTT assay would provide a fast, efficient, and quantitative method for evaluating HIV infected cells implanted intraperitoneally in mice.

Treatment of HIV-Infected Cells With Azidothymidine ("AZT")

An experiment was then set up to determine whether or not oral AZT treatment would alter the infection of HIV-inoculated CEM cells contained within encapsulation devices implanted intraperitoneally in Swiss mice.

The infected cells were prepared as described above. Additionally, 55 $\mu$l samples of the cells were diluted to 200 $\mu$l and analyzed for cell viability using the MTT.

Virus replication was again evaluated by measuring p24 antigen on the samples obtained from the devices after removal from the mice. A 5 $\mu$l aliquot of the cells was diluted 1:100 in Tris HCl (pH 7.4) and 200 $\mu$l was used for the assay. The p24 antigen was measured using Coulter Diagnostics ELISA kit (Miami, Fla.).

The virus infection was further evaluated by measuring reverse transcriptase levels in samples obtained from the devices. A 5 $\mu$l sample was diluted 1:10 with Tris-HCl (pH 7.4) and 25 $\mu$l of virus containing cells and supernatant were assayed.

The reverse transcriptase reactions, which were variously performed in microtiter plates and in 0.5 ml Eppendorf tubes, contained the following reagents: oligo dT, poly rA, Tris HCl (pH 7.4), DTT, $MgCl_2$, and EDTA. The reactions proceeded for 45–90 minutes at 37° C.

At the conclusion of the reaction, the total volume (25 $\mu$l) was spotted onto DE81 chromatography paper, washed five times with a large volume of 5% sodium phosphate buffer, two times with distilled water, and two times with ethanol. Following the ethanol wash the samples were air dried or dried under a heat lamp. The amount of incorporated radioactive thymidine was quantitated by liquid scintillation counting using a toluene-based fluor scintillation fluid.

AZT was dissolved in the water provided for the mice to drink. AZT oral treatment was begun 2 days prior to implantation in some of the mice. The remaining mice did not receive AZT.

The treatment with AZT was begun 2 days before implantation of the devices because the virus infection was initiated in the cells 2–4 hours prior to implantation. Further, in order for the drug to get to the CEM cells in the devices there must be time for an equilibration of the fluid (80 $\mu$l) in the device with the fluid in the peritoneal cavity. Therefore, the virus replication is probably underway long before appreciable amounts of drug penetrate the devices. As an alternative to the method used in this experiment, a very low number of chronically infected CEM cells mixed with a high number of susceptible fresh CEM cells can be used. For the uninfected CEM indicator cells to become infected, the chronically infected CEMs would have to produce and release virus into the supernatant fluid. The free virus would then infect the uninfected CEM cells and the two day pretreatment of test drug might not be necessary.

The devices were implanted intraperitoneally into mice, as described above, and were removed on the sixth day.

Upon microscopic examination, the "cell control" cells (i.e., no HIV, no AZT) looked normal as did the uninfected cells from mice treated with AZT. The "virus control" infected cells (i.e., with HIV, no AZT) all exhibited virus-induced cytopathic effect. The infected cells from AZT treated animals showed slight cytopathic effect. Eight of the encapsulation devices contained mouse cells or had burst during maintenance in the mice. The animals that were treated with AZT in drinking water did not show any signs of toxicity as indicated by appearance.

MTT assays were performed and the media control O.D. values were subtracted from all other values, as above. The O.D. values of both AZT-treated groups indicated that the drug was not toxic to the human cells used in the experiment. The infected, untreated (virus control) group, on the other hand, had O.D. values suggesting that only a few cells were viable. Finally, the O.D. values of the virus infected, AZT-treated groups had high O.D. values suggesting that most or all cells were viable at the time of assay.

The p24 antigen tests were performed on all samples and none of the uninfected cells had detectable levels of p24. The virus control group had a very high concentration of p24 suggesting an extensive degree of virus replication. Both treatment groups had significant reductions of p24 antigen (95 and 73.9% reduction). The high dose of AZT was more active than the lower dose.

The reverse transcriptase level was also measured. The uninfected cells only had background counts. As seen with p24 antigen, reverse transcriptase measurements after AZT treatment also bespoke a significant reduction in the amount of virus replication that occurred within the devices.

Thus, this experiment indicated that administration of AZT in the drinking water resulted in the metabolism and distribution of the drug to the fluid in the peritoneal cavity, since the animals treated with AZT had implanted CEM cells that displayed reduced cytopathic effect, p24 production, and reverse transcriptase production, and increased viability. This was demonstrative of the efficacy of the drug in this model system. Furthermore, AZT did not appear to be toxic to the animals or to the CEM cells enclosed in the encapsulation devices.

Capped Device

A double-skinned, smooth inner and outer lumen membrane of inner diameter 3.5 mm is prepared from KANEKA™ KLR resin as described in connection with the cylindrical device (supra). A 12% polyurethane/acetic acid (PU/AA) solution is also prepared as described above.

Titanium rings (2.0 mm long, 3.5 mm outer diameter, 3.0 mm inner diameter) are obtained and polished to remove any rough surface imperfections that can tear the membrane. The rings are dipped into PU/AA solution, coating the entire inner and outer surfaces of the rings. The polyurethane is allowed to cure for 1.5 hours.

The membrane is cut squarely to 13.5 mm length with caution to ensure a clean, non-feathered cut. The glycerine is removed from each end of the membrane by touching the end to a foam square saturated with 200 proof ethanol for a period of 3 minutes. The wetted length does not exceed 2 mm.

The membrane is allowed to dry for 20 minutes, until the ethanol treated end becomes white. The metal rings are then inserted into and aligned with the ends of membrane to make the ends rigid. The rings are sealed in place by applying a band of PU/AA solution with a syringe fitted with a fine-tipped applicator. The band is uniformly extended from the ethanol-treated end of the membrane to the PU/AA-treated tube end. The polyurethane is allowed to cure for 1.5 hours.

Two additional applications of PU/AA are made with 1.5 hour cures between applications. After the final application, the polyurethane is allowed to cure for a minimum of 16 hours.

The devices are then placed in 10 ml centrifuge tubes. The tubes are filled with WFI and capped. After about one hour, the tubes are drained and the device lumens are flushed with fresh WFI. The tubes are refilled with fresh WFI and allowed to sit for another 1.5 hours. This procedure is repeated for a total of five exchanges.

The tubes are then capped and sealed in plastic bags. The bags are double heat sealed and the bags and their contents are subjected to gamma sterilization (exposure range: 2.5–4.0 Mrads). The devices are removed from the tubes.

Two teflon caps having lips that fit snugly over the ends of the metal rings are obtained. One of the caps is snapped over one end of the device.

Cells are introduced into the lumen of the device through the non-capped opening.

The remaining cap is snapped over the open end of the device.

Device with Polyurethane Conduits

Double-skinned, smooth inner and outer lumen membranes prepared from KANEKA™ KLR resin as described in connection with the cylindrical device (supra) having inner diameters ranging from 1.5 to 3.5 mm were cut into segments of various lengths. One cut end of each segment was lightly touched to a sponge moistened with 200 proof ethanol, drawing the glycerine from the membrane (end 1–2 mm only) in preparation for treatment with polyurethane.

Once removed from the ethanol, the end was allowed to dry until it became white (about 10 to 60 minutes). The dried, deglycerinized end was dipped into a polyurethane/acetic acid solution to a depth of approximately 1.0 to 2.0 mm for about 60 seconds. Once removed from the solution, the excess solution was allowed to drain off and the lumen cleared if necessary to maintain the opening. The treated membrane was allowed to dry for 1.5 hours. During this time the acetic acid dissipated and the polyurethane became firm.

A snug fitting mandrel was inserted into the treated end. The polyurethane solution was applied using a fine-tipped pipette or a needle attached to a syringe. The treated end of each membrane and a 7–8 mm portion of the mandrel adjacent to the end of the membrane were treated with the PU. A total of three applications were made in this manner, with a 90 minute cure time between applications. The final application was allowed to cure overnight.

The polyurethane film was peeled away from the mandrel. The extension was trimmed with a razor or scissors to a length of approximately 5 mm.

The process was repeated for the second end, resulting in a length of membrane with a PU extension on each end.

A mechanical heat sealer was designed to seal the extension. The treated membranes were held so as to ensure consistent sealing distance away from the membrane. The devices were sealed approximately 1 mm away from the edge of the membrane. The excess length of membrane was trimmed away. The remaining end was left unsealed.

The finished devices were washed extensively with sterile water to remove glycerine from the membrane. The devices were placed in vials containing sterile water, sealed, and sterilized by gamma irradiation. The final, sterilized devices were removed from the vials, the water was removed from the lumen with a pipette, and the devices were filled.

Cells or other media or solution were inserted using a pipette or syringe; due caution was taken to ensure that the fill was not higher than the edge of the membrane, to leave the PU sealing area dry. once the devices were filled, the open end was sealed using a pair of smooth jawed forceps that have been flamed using a gas burner.

Bullet-Shaped Device

A device is made by spraying a membrane polymer onto a rigid, cup-shaped support, rather than by extrusion. The support is made of polyurethane to allow the membrane to be easily peeled away. The support includes a fitting on its open end to accept the cap for sealing. The resulting membrane therefore had a bullet-shaped bag form. This membrane offered the advantage of having only one end to seal. The use of the device is therefore simplified: bioactive materials are added, then the open end is capped.

Because there is only one end to seal, the length of the membrane could be shorter, as an extension for the first seal is not required. A further advantage is that the smooth end provide greater biocompatibility. Since only one end needs to be sealed, there is less handling and therefore less chance of contamination. If a bag-shaped device with a frame were desired, the membrane could be sprayed directly onto the frame.

Other Embodiments

It is to be understood that while the invention has been described in conjunction with the detailed description thereof, the foregoing description is intended to illustrate and not limit the scope of the appended claims. Other aspects, advantages, and modifications are within the scope of the following claims.

For example, cells that excrete beneficent proteins, such as enzymes or cytokines (e.g., insulin), can be encapsulated and implanted for treating numerous diseases, such as diabetes. Ordinarily, such cells would be rapidly killed and devoured by an immune response in the host; encapsulation of these cells with a biocompatible, semipermeable membrane, however, prevents diffusion of these proteins without induction of an immune response.

What is claimed is:

1. An empty device for receiving a bioactive agent, comprising:

a biocompatible and semi-permeable membrane having an inner surface and an outer surface, wherein said inner surface defines an enclosed space; said membrane also having one end that defines an opening for introducing the bioactive agent into said enclosed space; and a biocompatible adhesive in the general region of said opening to allow sealing of said opening after the introduction of the bioactive agent into said enclosed space, wherein said biocompatible adhesive is a heat sealable polymer conduit extending beyond said end of said membrane for a length sufficient to allow heat sealing of said conduit without causing said membrane to be contacted with a heated element in the heat sealing process; said conduit overlapping and being secured to a terminal portion of the outer surface of said membrane, wherein said device is configured to be placed in an animal and said membrane is in the form of a preformed bag.

2. The device of claim 1, wherein said membrane has a hydraulic permeability of 8–70 ml/min/m$^2$/mmHg and a molecular weight cut-off value of 20–150 Kdal.

3. The device of claim 2, wherein said membrane has a hydraulic permeability of 25–50 ml/min/m$^2$/mmHg.

* * * * *